United States Patent [19]

Bowman et al.

[11] 4,430,098
[45] Feb. 7, 1984

[54] APPARATUS FOR DEGASSING HEMODIALYSIS LIQUID AND THE LIKE

[76] Inventors: Donald B. Bowman, 7635 NW. McDonald Cir.; Charles J. Filz; James G. Osborn, both of 1930 SE. Stone St., all of Corvallis, Oreg. 97330

[21] Appl. No.: 181,107

[22] Filed: Aug. 25, 1980

Related U.S. Application Data

[62] Division of Ser. No. 669,903, Mar. 24, 1976, Pat. No. 4,325,715.

[51] Int. Cl.³ .............................................. B01D 31/00
[52] U.S. Cl. ...................................... 55/191; 210/188; 210/321.3
[58] Field of Search .................... 210/321.3, 188, 436, 210/497.1; 55/36, 386, 97, 191

[56] References Cited

U.S. PATENT DOCUMENTS

| | | | |
|---|---|---|---|
| 1,387,748 | 8/1921 | Wilson | 55/191 X |
| 3,463,615 | 8/1969 | Sochor | 55/386 X |
| 3,827,561 | 8/1974 | Serfass et al. | 210/436 X |
| 3,843,523 | 10/1974 | Dresen et al. | 210/497.1 X |
| 3,920,556 | 11/1975 | Bowman | 210/321.3 |

Primary Examiner—Frank A. Spear, Jr.
Attorney, Agent, or Firm—Delbert J. Barnard; Joan H. Pauly

[57] ABSTRACT

A gas-containing hemodialysis liquid is introduced into a helical coil of tubing formed from a hydrophobic material. Axial flow through the tubing is prevented and the hemodialysis liquid is pressure forced through the hydrophobic material, to free the gases from solution. Gases are released from the liquid through the hydrophobic material into an annular chamber surrounding the tubing.

10 Claims, 5 Drawing Figures

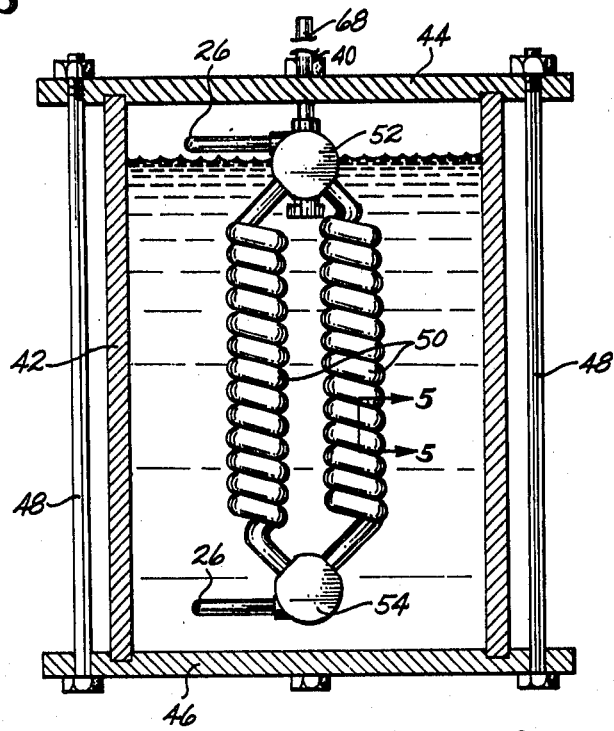
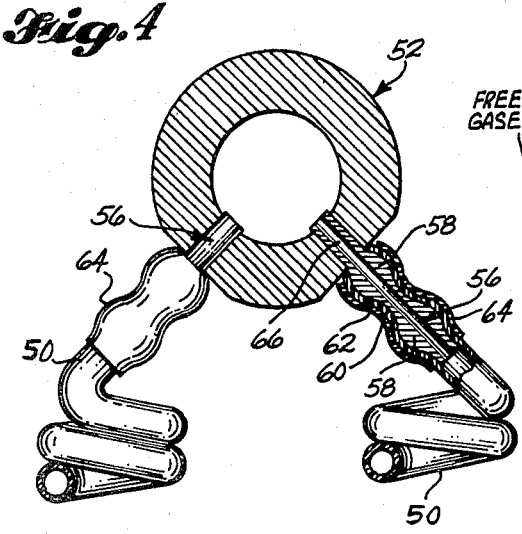
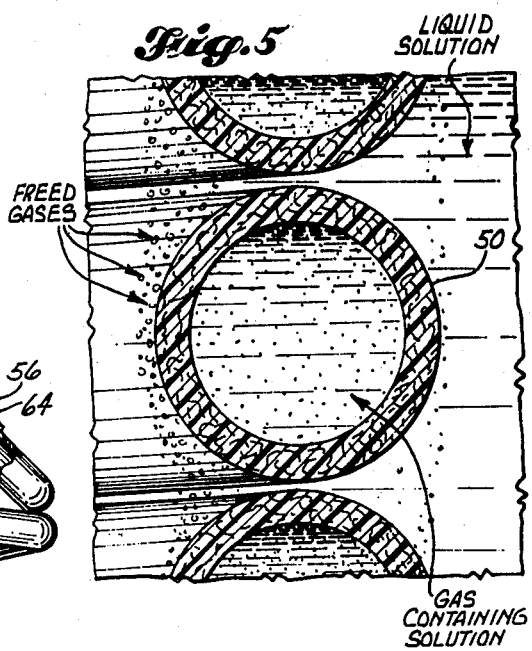

APPARATUS FOR DEGASSING HEMODIALYSIS LIQUID AND THE LIKE

This application is a division of U.S. application Ser. No. 669,903, filed Mar. 24, 1976, entitled Apparatus For Degassing Hemodialysis Liquid, and now U.S. Pat. No. 4,325,715, granted Apr. 20, 1982.

BACKGROUND OF THE INVENTION

1. Cross-Reference to Related Application

This application is related to my prior U.S. application Ser. No. 479,998, filed June 17, 1974 entitled Hemodialysis System, and now U.S. Pat. No. 3,920,556, granted Nov. 18, 1975. Specifically, the subject matter of this application supersedes the apparatus for removing gas bubbles from the hemodialysis solution disclosed by such patent.

2. Field of the Invention

This invention relates to apparatus for removing gases from liquids, and more particularly, it relates to apparatus for degassing a hemodialysis liquid.

3. Description of the Prior Art

My prior U.S. Pat. No. 3,515,275, granted Jan. 2, 1970, the several patents mentioned therein, and the prior art that was cited and considered by the Patent Office and listed at the end of the patent should be consulted for the purpose of properly evaluating the subject invention and putting it into proper perspective. The following additional patents relating to artificial kidneys or hemodialysis systems, should also be consulted: U.S. Pat. No. 3,352,779, granted Nov. 14, 1967, to Avery J. Austin and Robert S. Patch; U.S. Pat. No. 3,406,826, granted Oct. 22, 1968, to Charles B. Willock; U.S. Pat. No. 3,528,550, granted Sept. 15, 1970, to Christian Cappelen, Jr.; U.S. Pat. No. 3,598,727, granted Aug. 10, 1971, to Charles B. Willock; and U.S. Pat. No. 3,827,561, granted Aug. 6, 1974, to Earl J. Serfass, Edward R. Lindsay, Jr., Gene M. Holmes, James D. Aid and French Bishop, Jr. Several of these patents are concerned with the problems of removing gases from the hemodialysis solution prior to introduction of such solution into the hemodialyzer.

The present invention relates to novel way of utilizing a hydrophobic material for efficiently removing the unwanted air and other gases.

Additional U.S. patents which should be studied in conjunction with the subject invention, some of which involve the use of hydrophobic material, are: U.S. Pat. No. 3,463,615, granted Aug. 26, 1969, to Cestmir Sochor; U.S. Pat. No. 3,492,793, granted Feb. 3, 1970, to Pravin G. Bhuta and Robert L. Johnson; U.S. Pat. No. 3,523,408, granted Aug. 11, 1970, to David Rosenberg; U.S. Pat. No. 3,614,856, granted Oct. 26, 1971, to Manuel C. Sanz and John J. J. Staunton; U.S. Pat. No. 3,651,616, granted Mar. 28, 1972, to Alain Blanchard and Alphonse Faure; U.S. Pat. No. 3,665,680, granted May 30, 1972, to Gustav Heuser and U.S. Pat. No. 3,768,563, granted Oct. 30, 1973, to Robert C. Brumfield.

SUMMARY OF THE INVENTION

In accordance to the invention, a hydrophobic material is used in a manner contrary to its intended purpose. As explained in Column 2 of the aforementioned U.S. Pat. No. 3,523,408, a hydrophobic material is defined as a filter material that is not wetted by liquid and normally remains open for passage of gas. Normally the air or gas flows through such material and the liquid does not and it is in this manner that the air or gas is separated from the liquid.

In accordance with the present invention, a wall of hydrophobic material is provided across the path of flow of the hemodialysis liquid. The liquid is delivered against a wall of the hydrophobic material under sufficient pressure to cause it to flow through the wall. It has been found that the hydrophobic material will pass the liquid as well as the gases without destructive effects to the material. It has also been found that when the liquid is pressure fed through the hydrophobic material the gases are freed from the liquid so that they can be readily separated from the liquid downstream of the hydrophobic material.

In preferred form, the wall of hydrophobic material is provided in the form of at least one tubular coil. The liquid is introduced into the coil but prevented from flowing axially through the coil. Instead, the liquid is pressure fed laterally outwardly through the wall of the tubing into the surrounding region. In accordance with this aspect of the invention, a collection chamber may be provided about the tubing. The freed gases are removed from the upper portion of the collection chamber and the degassed liquid is removed from a lower portion of the chamber and delivered into the hemodialyzer, in the usual manner.

An important feature of the invention is that degassification is effectively achieved without the necessity of heating the hemodialysis solution above the body temperature in order to coalesce dissolved air into bubbles. Also, no separate bubble trap is required. The degasser functions as its own bubble trap.

These and other objects, features, advantages and characteristics of my invention will be better understood from the following detailed description of the preferred embodiment, with reference being made to the accompanying drawing.

DETAILED DESCRIPTION OF THE DRAWING

In the drawing like reference characters refer to like parts, and:

FIG. 3 is a view like FIG. 2, but taken at a right angle thereto, substantially along lines 3—3 of FIG. 2;

FIG. 4 is an enlarged scale sectional view, taken substantially along lines 4—4 of FIG. 2, showing a header connected to the coils of hydrophobic tubing, with some parts shown in elevation; and FIG. 5 is an enlarged scale cross sectional view of the hydrophobic tubing, illustrating the freeing of air as the solution is forced through the hydrophobic wall material.

DESCRIPTION OF THE PREFERRED EMBODIMENT

Figure 1:
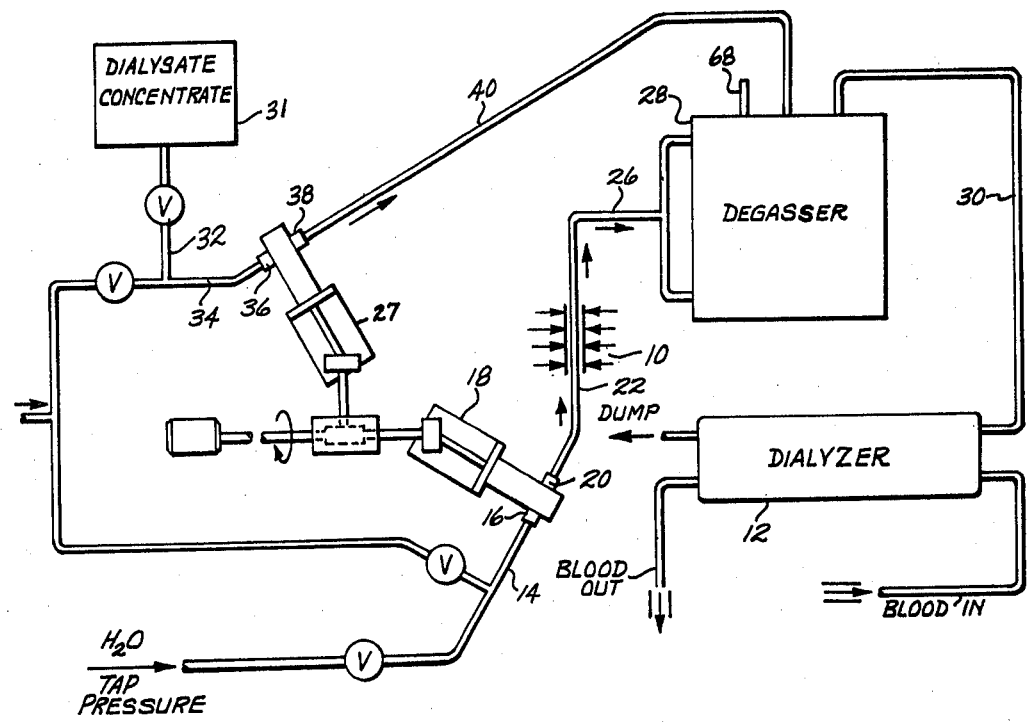
FIG. 1 is a flow diagram of a hemodialysis system employing degassing apparatus according to this invention.

FIG. 1 is a flow diagram of an artificial kidney or hemodialysis system of a type that is particularly suited for home use, and which includes an embodiment of the present invention.

Referring to FIG. 1, a stream of cold water (e.g. cold tap water) is directed through a conduit 14 leading to the inlet 16 of a first positive displacement pump 18.

The outlet 20 of pump 18 is connected to a conduit 22 which carries the water to a flow-through heater 10 in which it is heated to a proper temperature for its use in the dialyzer 12. Preferably, the water flows from heater 10 through a conduit 26 into the degassing apparatus 28.

A second pump 27 is used to pump the dialysate concentrate from a reservoir 31 through conduits 32, 34 to a pump inlet 36, and out through the pump outlet 38 into a conduit 40 which leads into the degassing apparatus 28.

As will become evident, the water and concentrate become mixed together in the degassing apparatus 28. A typical ratio of water to dialysate concentrate is 35:1, and as explained in my companion application Ser. No. 479,998, the proportioning function is performed by the pumps 18, 27. The degassing apparatus 28 functions to remove unwanted air and other gases from the solution. The degassed solution then flows from degasser 28 through line 30 in which it is subjected to the usual monitors (not shown), then into and through the hemodialyzer 12. In the hemodialyzer 12 the solution passes along one side of semi-permeable membranes in counter flow to the patient's blood which is flowing on the opposite side of the membrane. The cleansed blood is returned to the patient and the spent hemodialysis solution is dumped.

FIGS. 2-5 relate to preferred form of apparatus for degassing the hemodialysate concentrate. By way of typical and therefore non-limitative example, the apparatus may comprise a cylindrical side wall 42 and two end walls 44, 46 which are shown clamped in place at opposite ends of side wall 42 by means of a plurality of nut and bolt assemblies 48.

In basic terms, a wall of hydrophobic material is provided within housing 42, 44, 46. Gas-containing hemodialysis liquid is delivered under pressure against one side of such wall. The pressure level is sufficient to force the solution to flow through the wall. This results in the gases being freed from solution, so that downstream of such wall the gases can be easily removed from the liquid.

In the illustrated embodiment the liquid is water. However, it is within the scope of the invention for the water and concentrate to be mixed upstream of the degassing apparatus, with the resulting solution being the liquid. In the illustrated embodiment the wall of hydrophobic material is in the form of a plurality of coils 50 of hydrophobic tubing. A pair of headers or manifolds 52, 54 are spaced apart within housing 42, 44, 46. As best shown by FIG. 4, each header 52 (or 54) is provided with a short delivery duct 56 for connection to one end of each coil 50 (i.e. a duct 56 for each coil). Exteriorly, each delivery duct 56 may be formed to include alternating ridge and valley portions 58, 60. A mounting end portion 62 of a coil 50 is stretched over each delivery tube 56. A tubular retainer 64 may be provided around each end portion 62 and heat shrunk to confrom it in shape to the exterior configuration of the delivery tube 56. In the illustrated embodiment, the upper end portions are attached in this fashion to the header 52 and the lower end portions are attached to the header 54.

The coils 50 may include a stiff wire (not shown) skeleton for holding their shapes. The wire is stiff enough that when it is wound into a helical coil it maintains that form and in turn maintains the tubing in a helical coil form. The wire may be molded into a wall portion of the tubing material, or may even be inserted into the passageway of the tubing and then formed into a coil. By way of typical and therefore non-limitative example, the coils 50 may be formed from Gore-tex, a Trademark product of W. L. Gore & Associates, of Flagstaff, Ariz. Gore-tex comes in a coil form and includes a helical wire skeleton of the type described.

The gas-containing hemodialysis liquid from conduit 26 is delivered into both headers 52, 54 and from both headers 52, 54 flows into the coils 50 through both ends thereof. As should be readily apparent, this arrangement prevents the liquid from flowing axially through the hydrophobic tubing. The only way for the liquid to leave the tubing 50 is through the hydrophobic material which forms the tubing walls.

Referring again to FIG. 4, the relatively small diameter passageway 66 extending through each delivery tube 56 functions as a pressure reducing restriction. The water used in the system is tap water and when it reaches conduit 26 it is at a pressure substantially above atmospheric pressure. The flow restriction passageways 66 reduce the pressure to a desired level. According to the present invention, the gas-containing liquid is delivered into the coils 50 at a sufficient pressure that will cause such liquid to be pressure fed outwardly through the hydrophobic material forming the walls of the coils 50. It was found that this action caused the air and other trapped gases which were in the solution to be freed from the liquid, so that such gases could be readily removed from the liquid on the downstream side of the hydrophobic material. This phenomenon is graphically illustrated in FIG. 5. In this figure dashes are used for depicting the liquid both inside and outside of the tubing 50. Dots are used to depict the trapped gases in the liquid within the tubing and bubble-like circles are used to depict the freed gas in the liquid on the outside of the tubing. It was observed that in actual practice a substantial portion of the gas bubbles appeared to have passed through the inner wall portions of the coils 50 bordering the tunnel regions of the coils 50. An attempt has been made to illustrate this phenomenon in FIG. 5. The freed air bubbles rose in the liquid to the top of the chamber.

Figure 2:
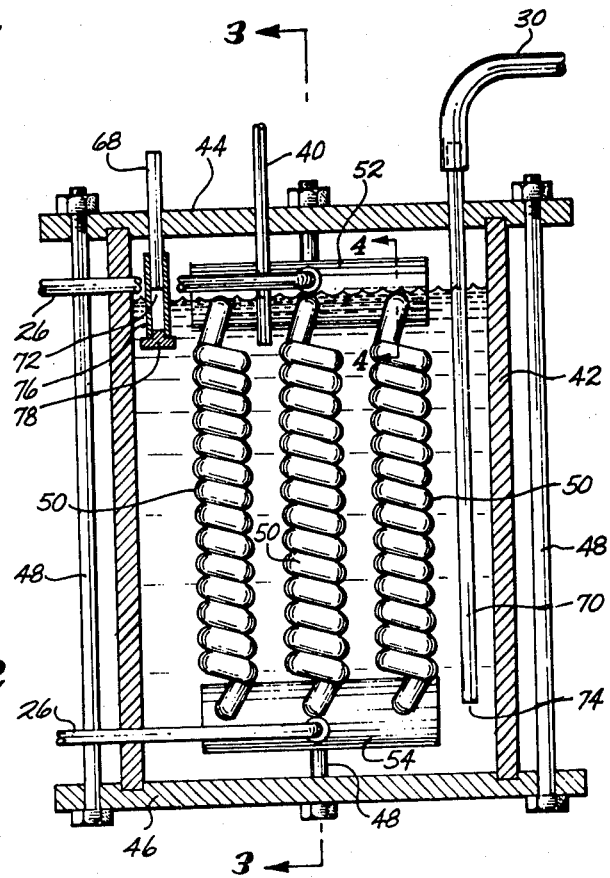
FIG. 2 is a longitudinal sectional view of the degassing apparatus with some internal components shown in section and others in elevation, for clarity of illustration.

In the illustrated embodiment the dialysate concentrate is delivered through tube 40 into the body of degassed liquid and mixing occurs within the chamber of housing 42, 44, 46. According to an aspect of the invention, an outlet tube 68 for the freed gases is arranged to lead outwardly from an upper portion of the chamber and an outlet tube 70 for degassed hemodialysis solution is arranged to lead outwardly from a lower portion of such chamber. As best shown by FIG. 2, both of the tubes 68, 70 extend through openings in the top wall 44. However, the inlet 72 for gas tube 68 is located closely adjacent top wall 44 whereas the inlet 74 for the liquid tube 70 is located closely adjacent the bottom wall 46.

As shown by FIG. 2, a short length 76 of hydrophobic tubing closed at its lower end by a suitable plug 78, may be connected to the inlet end portion of tube 68. This arrangement provides a cylindrical wall of hydrophobic material in the space between plug 78 and inlet 72 through which only freed gases can pass. If desired, the amount of gases removed from the gas-containing hemodialysis solution can be increased by connecting the tube 68 to a vacuum pump (not shown).

It is to be understood that the invention may be embodied in other specific forms of apparatus without departing from the spirit or basic characteristics of the invention. The illustrated and above described embodiments are to be considered in all respects as illustrative and not restrictive. The scope of the invention is to be determined by the appended claims rather than by the drawing and foregoing description. It is intended that all changes, modifications and/or adaptations which come within the meaning and range of equivalency of the claims are to be considered a part of the invention.

What is claimed is:

1. Apparatus for removing gases from a hemodialysis liquid prior to introduction of such liquid into a hemodialyzer, said apparatus comprising:
   wall means of filter material that is not wetted by liquid and which includes pores which normally remain open for passage of gas, defining a tubular coil having two ends;
   means for delivering a gas-containing hemodialysis liquid into the interior of said coil, through both ends of said coil, and against said wall means under sufficient pressure to force said liquid through said wall means, said gas being freed from the liquid as it passes through the wall means; and
   means for separating the freed gas from the hemodialysis liquid downstream of said wall means.

2. Apparatus according to claim 1, further comprising:
   liquid-and-gas impervious wall means defining a fluid chamber;
   said tubular coil being located within said fluid chamber;
   an outlet passageway for the freed gas leading outwardly from an upper portion of the chamber; and
   an outlet passageway for degassed hemodialysis liquid leading outwardly from a lower portion of said chamber.

3. Apparatus according to claim 2, further comprising vacuum means connected to said outlet passageway for freed gases, for facilitating removal of the freed gases.

4. Apparatus according to claim 1, wherein the wall means of filter material is in the form of a plurality of coils of hydrophobic tubing and said gas-containing hemodialysis liquid is introduced into the interior of each said coil.

5. Apparatus for removing gases from a hemodialysis liquid prior to introduction of such liquid into a hemodialyzer, said apparatus comprising:
   wall means of filter material that is not wetted by liquid and which includes bores which normally remain open for passage of gas, defining a tubular coil having at least one inlet;
   means for delivering a gas-containing hemodialysis liquid into the interior of said coil through said inlet, said means including a pressure restriction in said inlet for causing a pressure drop in the hemodialysis liquid, and said means delivering said liquid against said wall means under sufficient pressure to force said liquid through said wall means, said gas being freed from the liquid as it passes through the wall means; and
   means for separating the freed gas from the hemodialysis liquid downstream of said wall means.

6. Apparatus for removing gases from a hemodialysis liquid prior to introduction of such liquid into a hemodialyzer, said apparatus comprising:
   a wall of filter material that is not wetted by liquid and includes pores which normally remain open for passage of gas;
   means for delivering a gas-containing hemodialysis liquid against said wall under sufficient pressure to force said liquid through said wall, said gas being freed from said liquid as it passes through the wall;
   means for separating the freed gas from the hemodialysis liquid downstream of said wall;
   wherein said wall of filter material is in the form of a tubular coil and said liquid is introduced into the interior of said coil; and
   wherein the means for delivering a gas-containing hemodialysis liquid comprises a pair of spaced apart hollow chambers and conduit means for delivering the gas-containing hemodialysis liquid into said chambers, each said hollow chamber including a short delivery tube leading outwardly therefrom, with said tubular coil being disposed between said hollow chambers, with one of said delivery tubes being connected to one end of the tubular coil, and with the other being connected to the opposite end of said tubular coil.

7. Apparatus according to claim 6, wherein each said delivery tube includes a pressure reducing restriction, operable to reduce the pressure of the gas-containing hemodialysis liquid as it flows out from the associated hollow chamber into the tubular coil.

8. Apparatus according to claim 6, wherein each said delivery tube extends into its end portion of the tubular coil, and wherein the apparatus further includes means for clamping the end portions of the tubular coil onto said delivery tubes.

9. Apparatus for removing gases from a liquid, said apparatus comprising:
   a closed chamber bounded by a wall of filter material that is not wetted by liquid and includes pores which normally remain open for passage of gas;
   means for delivering a gas-containing liquid into said chamber and against said wall under sufficient pressure to force said liquid through said wall, said gas being freed from said liquid as it passes through the wall; and
   means for separating the freed gas from the liquid downstream of said wall;
   wherein said wall of filter material is in the form of a tubular coil, the interior of said coil is said closed chamber, and said gas-containing liquid is introduced into the interior of said coil; and
   wherein the means for delivering the gas-containing liquid into said coil delivers it into both ends of said coil.

10. Apparatus for removing gases from a liquid, said apparatus comprising:
    a closed chamber bounded by a wall of filter material that is not wetted by liquid and includes pores which normally remain open for passage of gas;
    means for delivering a gas-containing liquid into said chamber and against said wall under sufficient pressure to force said liquid through said wall, said gas being freed from said liquid as it passes through the wall; and
    means for separating the freed gas from the liquid downstream of said wall;
    wherein said wall of filter material is in the form of a tubular coil including at least one inlet, the interior of said coil is said closed chamber, and said gas-containing liquid is introduced through said inlet into the interior of said coil; and
    wherein said inlet is provided with a pressure restriction for causing a pressure drop in the liquid.

* * * * *

UNITED STATES PATENT AND TRADEMARK OFFICE
CERTIFICATE OF CORRECTION

PATENT NO. : 4,430,098
DATED : February 7, 1984
INVENTOR(S) : Donald B. Bowman; Charles J. Filz; James G. Osborn It is certified that error appears in the above-identified patent and that said Letters Patent are hereby corrected as shown below:

Column 5, line 46, "bores" should be --pores--.

Signed and Sealed this

Eighth Day of May 1984

[SEAL]

Attest:

GERALD J. MOSSINGHOFF

*Attesting Officer*         *Commissioner of Patents and Trademarks*